United States Patent [19]

Amick

[11] Patent Number: 5,023,275

[45] Date of Patent: Jun. 11, 1991

[54] S-SUBSTITUTED BETA-THIOACRYLAMIDE BIOCIDES AND FUNGICIDES

[75] Inventor: David R. Amick, Doylestown, Pa.

[73] Assignee: Rohm and Haas Company, Philadelphia, Pa.

[21] Appl. No.: 533,568

[22] Filed: Jun. 5, 1990

Related U.S. Application Data

[63] Continuation-in-part of Ser. No. 387,452, Jul. 28, 1989.

[51] Int. Cl.$^5$ .................. A61K 31/165; C07C 235/76
[52] U.S. Cl. ..................................... 514/627; 564/200
[58] Field of Search ........................ 564/200; 514/627

[56] References Cited

U.S. PATENT DOCUMENTS 3,914,301 10/1975 Miller et al. ..................... 564/200
4,014,679 3/1977 Perronnet et al. .................. 564/200

FOREIGN PATENT DOCUMENTS 2133450 1/1972 Fed. Rep. of Germany ...... 564/200

OTHER PUBLICATIONS

Crow, W., et al., "Isothiazole Chemistry", CA, 71, 3313f (1971).
W. D. Crow and I. Gosney, Aust J Chem. 22, 765–774 (1969).
W. D. Cow and I. Gosney, Tetrahedron, 26, 1463–1473 (1970).

*Primary Examiner*—Glennon H. Hollrah
*Attorney, Agent, or Firm*—Michael B. Fein

[57] ABSTRACT

S-substituted beta-thioacrylamide compounds have been discovered to be useful as biocides and fungicides. Compositions comprising the compound and isothiazolin-3-ones and/or carriers, methods of preparation of the compounds and methods of using the compounds and compositions are also disclosed.

7 Claims, No Drawings

S-SUBSTITUTED BETA-THIOACRYLAMIDE BIOCIDES AND FUNGICIDES

This application is a continuation-in-part of serial number 07/387,452 of July 28, 1989.

BACKGROUND OF THE INVENTION

1. Field of the Invention

This invention relates to biocides and fungicides.

2. Description of the Prior Art

The following references were considered pertinent, but do not describe or suggest the present invention: Miller, et al., U.S. Pat. No. 3,914,301 (Oct. 21, 1975), commonly assigned, and W. D. Crow and I. Gosney, Aust. J. Chem., 22, 765-774 (1969).

SUMMARY OF THE INVENTION

There is a need for alternative biocides and fungicides, especially improved ones.

It is therefore an object of the present invention to provide novel compounds which are useful in any locus subject to contamination by bacteria or fungi.

These objects and others as will become apparent from the following detailed description, are achieved by the present invention which in one aspect comprises a compound of the formula

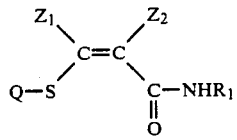

wherein $R_1$ is selected from unsubstituted or substituted aryl, alkaryl, or aralkyl, Q is

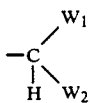

wherein $W_1$ and $W_2$ are independently selected electron withdrawing groups; and $Z_1$ and $Z_2$ are independently selected from hydrogen, halogen and ($C_1$-$C_4$) alkyl.

In another aspect the invention comprises the use of such a compound as a biocide or as a fungicide, and compositions comprising such compounds in fungicidally effective amount and in an agronomically acceptably carrier. In another aspect the invention comprises a method of controlling or inhibiting growth of bacteria in a locus comprising incorporating into or onto the locus a biocidally effective amount of the compound.

DETAILED DESCRIPTION OF THE INVENTION AND THE PREFERRED EMBODIMENTS

The novel compounds of the invention have been found to be useful as bactericides or as fungicides or both. The compounds of the invention have the formula

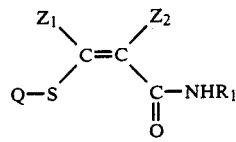

wherein $R_1$ is an unsubstituted or substituted aryl, alkaryl, or aralkyl group, Q is

wherein $W_1$ and $W_2$ are independently selected electron withdrawing groups, preferably carbonyl containing groups, and more preferably keto groups, especially acetyl; and $Z_1$ and $Z_2$ are independently selected from hydrogen, halogen and ($C_1$-$C_4$) alkyl.

Preferably $Z_1$ is halogen, especially chlorine and $Z_2$ is methyl. Q is preferably

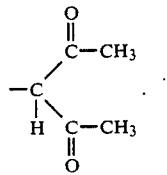

$R_1$ is preferably phenyl or chlorophenyl.

The beta-thioacrylamides of the invention can be used in any locus subject to contamination by bacteria or fungi. Typical loci subject to contamination by bacteria are in aqueous systems such as water cooling, laundry wash water, oil/water systems as cutting oils, oil fields and the like where microorganisms need to be killed or where their growth needs to be controlled.

Specific loci for bacteriostatic and fungistatic application include disinfectants, sanitizers, cleaners, deodorizers, liquid and powder soaps, skin removers, oil and grease removers, food processing chemicals, dairy chemicals, food preservatives, animal food preservatives, wood preservation, paint, lazures, stains, mildewcides, hospital and medical antiseptics, metal working fluids, cooling water, air washers, petroleum production, paper treatment, paper mill slimicides, petroleum products, adhesives, textiles, pigment slurries, latexes, leather and hide treatment, petroleum fuel, jet fuel, laundry sanitizers, agricultural formulations, inks, mining, nonwoven fabrics, petroleum storage, rubber, sugar processing, tobacco, swimming pools, cosmetics, toiletries, pharmaceuticals, chemical toilets, household laundry products, diesel fuel additives, waxes and polishes, electrodeposition systems, diagnostic products, medical devices, water purification systems, filtration systems, fishnets, marine antifoulants and other applications where water and organic materials come in contact under conditions which allow the growth of undesired microorganisms. Solutions of beta-thioacrylamides can also applied to a solid substrate, such as fabric, leather, or wood, as a preservative, or admixed with plastics. It is known in the art that the performance of biocides can frequently be enhanced by combination with one or more other biocides or fungicides. In fact, there have been numerous examples of synergistic combinations of biocides. Thus, other known biocides may be combined advantageously with the beta-thioacrylamides of this invention. See Industrial Antimicrobial Agents Encyclopedia of Chemical Technology, Volume 13, for a list of suitable other biocides. More specific industries and applications for the compounds are:

| Industry | Application |
|---|---|
| Adhesives, Sealants | Adhesives |
| | Caulks |
| | sealants |
| agriculture/food chain | adjuvant preservation |
| | agricultural active ingredient |
| | agricultural chemical preservative |
| | agricultural formulations preservation |
| | animal feed preservation |
| | dairy chemicals |
| | fertilizer preservation |
| | food preservation |
| | food processing chemicals |
| | grain preservation |
| | post-harvest produce protection |
| | sugar processing |
| | tobacco |
| Construction products | asphalt/concrete |
| | cement modifiers |
| | construction products |
| | roof mastics |
| | synthetic stucco |
| | wall mastics |
| | joint cement |
| Cosmetics and toiletries | Cosmetics |
| | raw materials for cosmetics, toiletries |
| | toiletries |
| Disinfectants, antiseptics | antiseptic |
| | disinfectant |
| Emulsions, dispersions | aqueous dispersions |
| | dispersed pigments |
| | latex |
| | photographic emulsions |
| | pigment slurries |
| | polymer latices |
| formulated household products | fabric softeners |
| | polishes |
| | waxes |
| | hand dish detergents |
| | raw materials |
| | liquid detergents |
| | hand soaps |
| Industrial processing, misc | electrodeposition paint, baths, rinses. |
| | electrodeposition pre-treatment, post rinses |
| | Industrial fluids preservation |
| | pasteurization baths |
| | process aid preservation |
| Industrial water treatment | air washers |
| | cooling towers |
| | cooling water |
| | water cooling |
| | preservation/treatment of wooden cooling tower slats and structural members |
| | can warmers |
| | brewery pasteurization |
| | closed loop water cooling systems |
| Laundry | household laundry products |
| | laundered goods |
| | laundry wash water |
| | sanitizers-laundry |
| Leather, Leather products | leather and hide |
| | leather and hide products |
| Lubricants, hydraulic aids | automotive lubricants and fluids |
| | conveyor lubricants |
| | greases |
| | hydraulic fluids |
| | lubricants |
| Medical devices | diagnostic enzymes |
| | diagnostic kits |
| | medical devices |
| metalworking & related app's | cutting fluids |
| | Metal cleaning |

-continued

| Industry | Application |
|---|---|
| | metalworking fluids |
| Odor control (active ingredient) | air conditioning |
| | animal bedding |
| | cat litter |
| | chemical toilet prep'ns |
| | deodorizers |
| | humidifiers |
| | industrial deodorants |
| | sanitary formulations |
| | toilet bowls |
| Paints and coatings coating | emulsions |
| | paints |
| Paper and wood pulp, their products | absorbant materials of paper and wood pulp |
| | packaging materials of paper and wood pulp |
| | paper |
| | paper products |
| | paper treatment |
| | soap wrap |
| | wood pulp |
| | wood pulp products |
| paper mill | paper mill slimicides |
| | pulp and paper slurries |
| Petroleum refining, fuels | aviation fuels (jet fuel, aviation gas) |
| | crude oils |
| | burner, diesel and turbine fuel oils |
| | coal slurries |
| | diesel fuel additives |
| | diesel fuels |
| | fuels |
| | gasoline |
| | heating oils |
| | hydrocarbons |
| | Kerosene |
| | liquefied petroleum gas |
| | petrochemical feedstocks |
| | petroleum products, storage, transportation and production |
| | recycled petroleum products |
| | residual fuel oils |
| | turbine oils |
| Photographic Chemicals and process | Photographic processing - wash water, rinses |
| | photoprocessing |
| | Photoplate processing chemicals (developers, stabilizers etc) |
| Printing | Fountain solutions (printing) |
| | Ink components (pigments, resins, solvents, etc) |
| | Inks |
| sanitizers (active) | sanitizers |
| | sanitizers-dairy |
| | sanitizers-dental |
| | sanitizers-fermentation |
| | sanitizers-food preparation |
| | sanitizers-food processing |
| | sanitizers-medical |
| | sanitizers-rendering |
| | sanitizers-veterinary |
| Soaps, detergents, cleaners | cleaners |
| | detergents |
| | household cleaners |
| | industrial cleaners |
| | liquid soaps |
| | oil and grease remover |
| | powdered soaps |
| | raw materials for cleaning products |
| | soaps |
| | surfactants |
| Textiles, textile products | bonded fabrics |
| | burlap |
| | canvas |
| | canvas goods |
| | carpet backing |
| | carpets |
| | clothing |
| | coated fabrics |
| | curtains |
| | draperies |
| | engineering textiles |

| Industry | Application |
|---|---|
| | fibers |
| | geotextiles |
| | goods made of textiles |
| | knitted fabrics |
| | nets |
| | nonwoven fabrics |
| | rope |
| | rugs |
| | textile accessories |
| | textile products |
| | textiles |
| | upholstery |
| | woven fabrics |
| | yarn |
| Textile processing | dye fixatives |
| | dyes |
| | fiber lubricants |
| | hand modifiers |
| | sizes |
| | Textile processing fluids |
| Therapeutic (active or preservative) | animal health/veterinary |
| | aquaculture |
| | dental |
| | human health |
| | pharmaceutical/therapeutic |
| water purification | charcoal beds |
| | deionization resins |
| | filters |
| | membranes |
| | reverse osmosis membranes |
| | ultrafilters |
| | Water purification |
| | water purification pipes, tubing |
| wood applications | lazures (wood stains) |
| | wood |
| | wood products |
| Miscellaneous | alcohols |
| | bedding incorporating water or gels |
| | ceramic |
| | contact lens cases-leaching |
| | electronic circuitry |
| | electronics chemicals |
| | enzymes-food production |
| | enzymes |
| | enzymes-industrial |
| | gel cushions |
| | marine antifoulants |
| | mildewcides |
| | wood |
| | plastics |
| | laundry |
| | mining |
| | natural rubber latex |
| | oil field injection waters including enhanced recover injection fluids, drilling, fracturing and completion fluids |
| | pipes |
| | plastics |
| | polymer systems |
| | polymers and resins (synthetic and natural) |
| | reagent preservation |
| | rubber |
| | rubber products |
| | skin remover |
| | solid protective/decorative films |
| | stains |
| | swimming pools |
| | waste treatment |
| | water beds |

The beta-thioacrylamide compounds of the invention can be applied as fungicidal sprays by methods commonly employed, such as conventional high-gallonage hydraulic sprays, low-gallonage sprays, airblast, aerial sprays and dusts. The dilution and rate of application will depend upon the type of equipment employed, the method and frequency of application desired and diseases to be controlled, but the effective amount for application is usually from about 5 grams (gm) to about 22 kilograms (kg), preferably from about 0.010 to about 1.0 kg per hectare.

As a seed protectant, the amount of fungicide coated on the seed is usually at a dosage rate of about 0.0001 to about 10 grams (gm) and preferably from about 0.1 to about 10 gm per 1 kilogram of seed. As a soil fungicide the beta-thioacrylamides can be incorporated in the soil or applied to the surface usually at a rate of 0.01 to about 22 kg, preferably about 0.05 to about 11 kg and more preferably from about 0.1 to about 3.3 kg per hectare. As a foliar fungicide the beta-thioacrylamides can be applied at a rate of from about 0.01 to about 11 kg, preferably from about 0.02 to about 5.5 kg and more preferably from about 0.1 to about 3.3 kg per hectare.

The present invention is useful for the control of fungi and can be utilized at various loci such as the seed, the soil or the foliage. For such purposes these compounds can be used in the technical or pure form as prepared, as solutions or as formulations. The compounds are usually taken up in a carrier or are formulated so as to render them suitable for subsequent dissemination as fungicides. For example, these beta-thioacrylamides can be formulated as wettable powders, emulsifiable concentrates, dusts, granular formulations, aerosols, or flowable emulsion concentrates. In such formulations, the beta-thioacrylamides are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art can be found in *McCutcheon's Emulsifiers and Detergents, McCutcheon's Emulsifiers and Detergents/Functional Materials* and *McCutcheon's Functional Materials* all published annually by McCutcheon Division of MC Publishing Company (New Jersey). In general, the beta-thioacrylamides of this invention can be dissolved in appropriate solvents such as acetone, methanol, ethanol, dimethylformamide or dimethyl sulfoxide and such solutions extended with water. The concentrations of the solution can vary from 1% to 90% with a preferred range being 5 to 50% (weight percentage). For the preparation of emulsifiable concentrates, the beta-thioacrylamides can be dissolved in suitable organic solvents or a mixture of solvents, together with an emulsifying agent which permits dispersion of the fungicide in water. The concentration of the active ingredient in emulsifiable concentrates is usually 10% to 90% and in flowable emulsion concentrates, this can be as high as 75% (weight percent). Water based flowable formulations of the beta-thioacrylamides can be prepared with a concentration of active ingredients in the range of 5 to 70% by weight, preferably 20 to 50% by weight.

A typical flowable formulation is prepared by wet-milling a mixture of 35 parts of beta-thioacrylamides, 10 parts of Barden clay, 4 parts of sodium lignosulfonate, 1 part of an anionic wetting agent and 50 parts of water.

Wettable powders suitable for spraying can be prepared by admixing the beta-thioacrylamide compound with a finely divided solid, such as clays, inorganic silicates and carbonates, and silicas and incorporating wetting agents, sticking agents, and/or dispersing agents in such mixtures. The concentration of active ingredients in such formulations is usually in the range of 5% to 98%, preferably 40% to 75% (weight percent), optional by blending 50 parts of an active ingredient selected from the S-substituted beta-thioacrylamides of Examples 1-7, 45 parts of a synthetic precipitated hydrated silicon dioxide sold under the trademark Hi-Sil, 1 part of an anionic naphthalenic sulfonate wetting agent and 4 parts of sodium lignosulfonate (Marasperse N-22). In another preparation of a kaolin type (Barden) clay is used in place of the Hi-Sil in the above wettable powder and in another such preparation 25% of the Hi-Sil is replaced with a synthetic sodium silico aluminate sold under the trademark Zeolex 7. Dusts are prepared by mixing the amides and salts and complexes thereof with finely divided inert solids which can be organic or inorganic in nature. Materials useful for this purpose include botanical flours, silicas, silicates, carbonates, talc and clays. One convenient method of preparing a dust is to dilute a wettable powder with a finely divided carrier. Dust concentrates containing 20% to 80% (weight percent) of the active ingredient are commonly made and are subsequently diluted to 1% to 10% use concentration.

The compounds of the present invention may also be utilized in combination with other fungicides such as:

(a) dithiocarbamates and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb), zinc propylenebisdithiocarbamate (propineb), sodium methyldithiocarbamate (metham), tetramethylthiuram disulfide (thiram), the complex of zineb and polyethylene thiuram disulfide, 3,5-dimethyl-1,3,5-2H-tetrahydrothiadiazine-2-thione (dazomet); and mixtures of these and mixtures with copper salts;

(b) nitrophenol derivatives such as: dinitro-(1-methylheptyl)phenyl crotonate (dinocap), 2-sec-butyl-4,6-dinitrophenyl-3,3-dimethylacrylate (binapacryl), and 2-sec-butyl-4,6-dinitrophenyl isopropyl carbonate;

(c) heterocyclic structures such as: Systhane (a registered trademark of Rohm and Haas for myclobutanil), triademifon, N-trichloromethylthiotetrahydrophthalimide (captan), N-trichloromethylthiophthalimide (folpet), 2-heptadecyl-2-imidazole acetate (glyodine), 2-octylisothiazolone-3, 2,4-dichloro-6-(o-chloroanilino)-s-triazine, diethyl phthalimidophosphorothioate, 4-butyl-1,2,4-triazole, 5-amino-1-[bis(dimethylamino)phosphinyl]-3-phenyl-1,2,4-triazole, 5-ethoxy-3-trichloromethyl-1,2,4-thiadiazole, 2,3-dicyano-1,4-dithiaanthraquinone (dithianon), 1,3-dithiolo-[4,5-b]quinoxaline-2-thione (thioquinox), methyl 1-(butylcarbamoyl)-2benzimidazole carbamate (benomyl), 2,4'-(thiazolyl) benzimidazole (thiabendazole), 4-(2-chlorophenylhydrazono)-3-methyl-5-isoxazolone, 3-(3,5-dichlorophenyl)-5-ethenyl-5-methyl-2,4-oxazolidinedione (vinclozolin), 3-(3,5-dichlorophenyl)-N-(1-methylethyl)-2,4-di-alphaoxo-1-imidazolinecarboxamide (dichlorophenyl)-1,2-dimethylcyclopropane-1,2-dicarboximide (procymidone), beta-(4-chlorophenoxy)-alpha-(1,1-dimethylethyl)-1H-1,2,4-trizole-1-ethanol (triadimenol), 1-(4-chlorophenoxy)-3,3-dimethyl-1-(1H-1,2,4-triazol-1-yl)-2-butanone (triadimefon), beta-[(1,1'-biphenyl)-4-yloxy]-alpha-(1,1-dimethylethyl)-1H-1,2,4-triazole-1ethanol (bitertanol), 2,3-dichloro-N-(4-fluorophenyl)maleimide (fluoroimide), 1-[2-(2,4-dichlorophenyl)-4-propyl-1,3-dioxolan-2-yl-methyl]-1H-1,2,4-triazole, pyridine-2-thiol-1-oxide, 8-hydroxyquinoline sulfate and metal salts thereof, 2,3-dihydro-5-carboxanilido-6-methyl-1,4-oxathiin-4,4-dioxide, 2,3-dihydro-5-carboxanilido-6-methyl-1,4-oxathiin, alpha-(phenyl)-alpha-(2,14-dichlorophenyl)-5-pyrimidinyl-methanol (triarimol), cis-N[(1,1,2,2-tetrachloroethyl)thio]-4-cyclohexene-1,2-dicarboximide, 3-[2-(3,5-dimethyl-2-oxycyclohexyl)-2-hydroxy]-glutarimide (cycloheximide), dehydroacetic acid, N-(1,1,2,2-tetrachloroethylthio)-3a,4,7,7a-tetrahydrophthalimide (captafol), 5-butyl-2-ethylamino-4-hydroxy-6-methyl-pyrimidine (ethirimol), acetate of 4-cyclodecyl-2,6-dimethyl-morpholine (dodemorph), and 6-methyl-2-oxo-1,3-dithiolo[4,5-b]-quinoxaline (quinomethionate);

(d) miscellaneous halogenated fungicides such as: tetrachloro-p-benzoquinone (chloranil), 2-3-dichloro-1,4-naphthoquinone (dichlone), 1,4-dichloro-2,5-dimethoxybenzene (chlorneb), 3,5,6-trichloro-o-anisic acid (tricamba), 2,4,5,6-tetrachloroisophthalonitril (TCPN), 2,6-dichloro-4-nitroaniline (dichloran), 2-chloro-1-nitropropane, polychloronitrobenzenes such as: pentachloronitrobenzene (PCNB) and tetrafluorodichloroacetone;

(e) fungicidal antibiotics such as: griseofulvin, kasugamycin and streptomycin;

(f) copper-based fungicides such as: copper hydroxide, cuprous oxide, basic cupric chloride, basic copper carbonate, copper terphthalate, copper naphthenate and Bordeaux mixture; and (g) miscellaneous fungicides such as: diphenyl, sultone, dodecylguanidine acetate (dodine), phenylmercuric acetate, N-ethylmercuri-1,2,3,6-tetrahydro-3,6-endomethano-3,4,5,6,7,7-hexachlorophth alimide, p-dimethylaminobenzene sodium sulfonate, methyl isothiocyanate, 1-thiocyano-2,4-dinitrobenzene, 1-phenylthiosemicarbazide, nickel-containing compounds, calcium cyanamide, lime sulfur, 1,2-bis(3-methoxycarbonyl-2-thioureido) benzene (thiophanate-methyl).

All of the novel S-substituted beta-thioacrylamides of the invention can be prepared by reacting an unsubstituted or substituted 4-isothiazolin-3-one with a suitable nucleophilic reagent. This reaction can be schematically represented as follows:

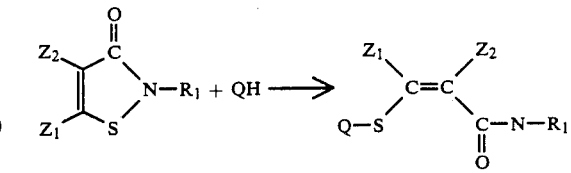

in which QH represents a typical nucleophilic reagent, for which Q is defined as:

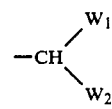

wherein $W_1$ and $W_2$ are independently selected electron withdrawing groups, $R_1$ is an unsubstituted or substituted aryl, alkaryl, or aralkyl group, and $Z_1$ and $Z_2$ are independently selected from hydrogen, halogen, and $(C_1-C_4)$alkyl groups. A preferred nucleophilic agent which can be used to cleave the 4-isothiazolin-3-one ring is a beta-diketone, especially 2,4-pentanedione.

In preparing the compounds of the invention, equimolar amounts of the 4-isothiazolin-3-one and the nucleophilic reagent are generally used. The convenient in-situ formation of sodium ethoxide from sodium metal in absolute ethanol can be advantageously used to facilitate the reaction between the 4-isothiazolin-3-one and the nucleophilic reagent by allowing the abstraction of the proton from the Q-H nucleophilic reagent to take place. The reaction between the nucleophilic reagent and the 4-isothiazolin-3-one is generally carried out at a temperature of about 0° C. to about 100° C., and preferably below 30° C. in that range. Various organic solvents can be used in carrying out the reaction, if desired, with an alcoholic solvent being preferred. However, any solvent or mixture of solvents which will not interfere with the reaction can be used. Under high pH conditions this reaction is reversable, resulting in compositions comprising both the compounds and the 4-isothiazolin-3-one percurser.

All of the 4-isothiazolin-3-one intermediates can be prepared by the cyclization of a substituted disulfidediamide having the formula:

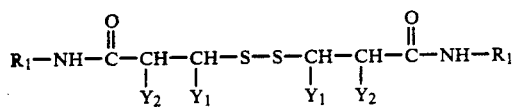

wherein $Y_1$ and $Y_2$ are hydrogen or $(C_1-C_4)$alkyl groups and $R_1$ is defined as above. The cyclization is accomplished by reacting the disulfidediamide with a halogenating agent. Any halogenating agent can be employed in this reaction, with chlorine and sulfuryl chloride being preferred. Cyclization of the disulfidediamide will take place when 3 mole equivalents of halogenating agent/mole equivalent of disulfidediamide are employed in the reaction. By providing an excess of halogenating agent, the 4-isothiazolin-3-one may be halogenated at the 4- and/or 5-positions of the ring. Where 5 mole equivalents of halogenating agent are available, mono-halogenation can take place. For dihalogenation, 7 mole equivalents of halogenating agent are required. The cyclization process will proceed over a broad temperature range and temperature is not critical to the reaction. Generally, the cyclization will be carried out in the range of $-10°$ C. to 100° C. The reaction is carried out in an inert non-aqueous solvent, such as ethyl acetate, ethylene dichloride, benzene, toluene, or xylene.

The following examples will further illustrate this invention, but are not intended to limit it in any way. All parts and percentages are by weight and all temperatures in degrees Centigrade, unless otherwise stated.

EXAMPLES

EXAMPLE 1

Synthesis of N-(p-Chlorophenyl)-2-methyl-3-chloro-cis-3-thio-(1-acetylpropan-2-on-1-yl) acrylamide A. To a 500 ml, 4-neck flask equipped with a mechanical stirrer, addition funnel, and a thermometer was placed 80 ml of ethyl acetate which was cooled to 0° C. Concurrently, 12.0 g (0.026 mol) of N,N'-bis-(p-chlorophenyl)-3,3'-dithiodiisobutyramide and 17.7 g (0.131 mol) of sulfuryl chloride then were added, both in 24 equal portions with stirring over a one hour period. After allowing the resulting mixture to warm to room temperature, the yellowish solution was concentrated under reduced pressure. The solid residue was recrystallized from 2-propanol to give 6.1 g (89% yield) of 2-(p-chlorophenyl)-4-methyl-5-chloro-4-isothiazolin-3-one intermediate as white needles whose m.p. = 104.5°–106° C.

B. To a dry, nitrogen purged 500 ml three-necked flask, equipped with a condenser, magnetic stirring bar, and a thermometer was added 75 ml of absolute ethanol. Freshly cut sodium metal (0.53 gm, 0.023 mol) was added in pieces with stirring at such a rate that the temperature of the mixture remained below 35° C. When all the sodium had dissolved, 2.31 gm (0.023 mol) of 2,4-pentanedione was added dropwise over a ten minute period with stirring. After allowing the solution to stir for 15 minutes, 6.0 gm (0.023 mol) of 2-(p-chlorophenyl)-4-methyl-5-chloro-4-isothiazolin-3-one in 60 ml of warm absolute ethanol was added over 20 minutes, keeping the temperature of the reaction mixture below 30° C. The mixture was stirred for an additional one hour and then poured into an ice-cold, 2N HCl solution with stirring. The solid precipitate was removed by filtration and washed three times with fresh water. The solid was dried under vacuum at 40° C. to give 7.8 gm (93.5% yield) of product which recrystallized from absolute ethanol as white, cottony needles; mp 164°–166° C.; IR (KBr): 3300 cm$^{-1}$ (NH), 1660 cm$^{-1}$ (C=O); NMR (CDCl$_3$): 2.2 ppm (s,CH$_3$), 2.4 ppm (s,2CH$_3$), 7.2–7.6 ppm (m, 5H, aromatic and NH), 17.3 ppm (s, CH). Melting point was 164°–166° C.

EXAMPLES 2–7

In a like manner other compounds having the general formula

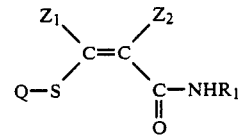

were prepared, wherein $R_1$, Q, $Z_1$ and $Z_2$, for each compound were as shown in Table 1, and were identified as indicated in said Table 1.

The intermediates for Examples 2–7 were prepared as follows:

A. Preparation of 2-Benzyl-4-isothiazolin-3-one Intermediate for Example 2

To a suspension of 58.2 g (0.15 mol) of N,N'-bis-benzyl-3,3'-dithiodipropionamide in 500 ml of ethylene dichloride at 10–15° C. was added dropwise 63.6 g (0.473 mol) of sulfuryl chloride. A clear, light amber solution resulted. After stirring overnight, the solution was concentrated to give about one half volume. Cream-colored solid separated and was collected by filtration, yielding 36.1 g of 2-benzyl-4-isothiazolin-3-one hydrochloride salt; 1.5 g of additional solid separated in the filtrate but proved to be starting material. The filtrate was further evaporated to a brown oil. The oil was redissolved in benzene, treated with decolorizing carbon, and evaporated once again. The resulting light amber oil solidified on standing. This light tan solid was recrystallized from heptane giving 8.0 g(12% yield) of white crystals of 2-benzyl-5-chloro-4-isothiazolin-3-one hydrochloride salt whose m.p. was 58°–59° C. The hydrochloride of the unchlorinated benzyl compound was converted to free base by trituration with water and was dried under vacuum to give 27.0 g (47% yield) of the 2-benzyl-4-isothiazolin-3-one intermediate, m.p.=78°-80° C.

B. Preparation of 2-(Beta-phenethyl)-4-isothiazolin-3-one Intermediate for Example 3

To a slurry of 103.9 g (0.25 mol) of N,N'-bis-(beta-phenethyl)-3,3'-dithiodipropionamide in 1000 ml of ethylene dichloride at 10-15° C. was added 101.3 g (0.75 mol) of sulfuryl chloride over a one hour period. After the addition, the mixture was allowed to warm to room temperature. The yellowish slurry mixture was concentrated to remove about two-thirds of the ethylene dichloride and the separated solid mass was removed by filtration and washed with ether. The solid was added to a mixture of 350 ml of water and 200 ml of chloroform. Solid sodium bicarbonate was added in portions with stirring until the aqueous phase was at pH 7-8. The layers were separated and the aqueous phase extracted with additional chloroform. The combined chloroform layers were dried over magnesium sulfate and concentrated to give a white solid residue which was recrystallized from a benzene/hexane mixture to give 44.8 g (44% yield) of the 2-(beta-phenethyl)-4-isothiazolin-3-one intermediate whose m.p. was 76°-78° C.

C. Preparation of 2-(p-Chlorobenzyl)-4-isothiazolin-3-one Intermediate for Example 4

To a slurry of 292.0 g (0.639 mol) of N,N'-bis-(4-chlorobenzyl)-3,3'-dithiodipropionamide in 2 liters of ethyl acetate was added 136.0 g (1.9717 mole) of chlorine in one hour, during which the reaction temperature rose to 47° C. The mixture was allowed to cool to room temperature, degassed, and then cooled to 10° C. The solid was removed by filtration, triturated with 200 ml of water, filtered, and dried. The dried solid was dissolved in 500 ml of boiling ethyl acetate and filtered to remove unreacted amide starting material. The ethyl acetate solution, on cooling, deposited a crystalline solid which was filtered and dried to give 132.2 g (46% yield) of the 2-(p-chlorobenzyl)-4-isothiazolin-3-one intermediate with a m.p.=88°-90° C.

D. Preparation of 2-Phenyl-4-methyl-5-chloro-4-isothiazolin-3-one Intermediate for Example 5

To 400 ml of ethyl acetate at 0° C. was added, during a one hour period, 155.2 g (0.4 mol) of N,N'-bis-phenyl-3,3'-dithiodiisobutyramide in 40 equal portions and 116.5 g (1.64 mol) of chlorine. The temperature was maintained at 0°-5° C. during the additions. The mixture was then allowed to warm to 15° C. The solution was then evaporated under reduced pressure, leaving a brown oil which partially solidified on standing. This material was dissolved in warm ethanol. On cooling, pink solid separated which was removed by filtration. The filtrate was evaporated to a dark oil. The oil was extracted with ether. Evaporation of the ether gave 112.7 g of a yellow mush. Three grams of this mush was chromatographed on a silica dry column developed with toluene. The main fraction (1.92 g), with a R value of approximately 0.7, was extracted from the silica with ether which was then evaporated. On standing, the residual oil solidified. This material was recrystallized from ethanol to give the cream-colored 2-phenyl-4-methyl-5-chloro-4-isothiazolin-3-one intermediate whose m.p.=60°-68° C.

E. Preparation of 2-(p-Chlorophenyl)-5-chloro-4-isothiazolin-3-one Intermediate for Example 6

To a suspension of 21 g (0.05 mol) of N,N'-bis-(p-chlorophenyl)-3,3'-dithiodipropionamide in 75 ml of ethyl acetate at 15° C. was added 18.6 g (0.26 mol) of chlorine over a 30 minute period. When addition was complete, the mixture was allowed to stand for several hours and then filtered. The collected solid was triturated with methanol and yielded a white solid. This material was crystallized from 140 ml of toluene with decolorization, using activated carbon, to give 5.82 g (19.5% yield) of the 2-(p-chlorophenyl)-5-chloro-4-isothiazolin-3-one intermediate whose m.p.=117°-119° C.

F. Preparation of 2-(p-Chlorophenyl)-4-methyl-4-isothiazolin-3-one Intermediate for Example 7

In a 2-liter flask equipped with a mechanical stirrer, two addition funnels, and a thermometer was placed one liter of ethyl acetate which was cooled to −5° to 0° C. Concurrently, N,N,'-bis-(p-chlorophenyl)-3,3'-dithiodiisobutyramide (116.3 g, 0.254 mol), sulfuryl chloride (141.7 g, 105 mol), and pyridine (40.0 g, 0.05 mol) were added over a 75 minute period while maintaining the temperature at 0° C. The mixture was allowed to warm to room temperature and then cooled back to −40° C. using a dry-ice bath. The solid precipitate was removed by filtration, washed with cold ethyl acetate, triturated with one liter of water, refiltered, and dried to give 46 g of 2-(p-chlorophenyl)-4-methyl-4-isothiazolin-3-one and 2-(p-chlorophenyl)-4-methyl-5-chloro-4-isothiazolin-3-one in a 2/1 mixture ratio. The dried solid mixture, 45.5 g, and sulfuryl chloride, 19.0 g (0.135 mol) were added concurrently to 300 ml of ethyl acetate at 0° C. over a one hour period. After the addition, the mixture was allowed to warm to room temperature and stirred overnight. The solid suspension was removed by filtration and treated with sodium bicarbonate solution. The treated solid was removed, dried, and recrystallized from 2-propanol to give 9.5 g of 2-(p-chlorophenyl)-4-methyl-4-isothiazolin-3-one intermediate whose m.p.=157°-159° C.

TABLE 1

| | Substituents and M.P.'s for Examples 2-7 | | | | |
| --- | --- | --- | --- | --- | --- |
| Example | Melting Point (°C.) | $R_1$ | $Z_1$ | $Z_2$ | O |
| 2 | 143.5-145 | —CH$_2\phi$ | —H | —H | —CH(COCH$_3$)$_2$ |
| 3 | 136-139 | —CH$_2$CH$_2\phi$ | —H | —H | —CH(COCH$_3$)$_2$ |
| 4 | 134-137 | —CH$_2$—C$_6$H$_4$—Cl | —H | —H | —CH(COCH$_3$)$_2$ |
| 5 | 107-112 | —$\phi$ | —Cl | —CH$_3$ | —CH(COCH$_3$)$_2$ |

TABLE 1-continued

Substituents and M.P.'s for Examples 2-7

| Example | Melting Point (°C.) | R₁ | Z₁ | Z₂ | Q |
|---|---|---|---|---|---|
| 6 | 164–166 | 4-Cl-phenyl | —Cl | —H | —CH(COCH₃)₂ |
| 7 | 120–125 | 4-Cl-phenyl | —H | —CH₃ | —CH(COCH₃)₂ |

TABLE 2

Starting Materials for Examples 2-7

| Example | Starting Isothiazolone |
|---|---|
| 2 | 2-benzyl-4-isothiazolin-3-one |
| 3 | 2-(beta-phenethyl)-4-isothiazolin-3-one |
| 4 | 2-(p-chlorobenzyl)-4-isothiazolin-3-one |
| 5 | 2-phenyl-4-methyl-5-chloro-4-isothiazolin-3-one |
| 6 | 2-(p-chlorophenyl)-5-chloro-4-isothiazolin-3-one |
| 7 | 2-(p-chlorophenyl)-4-methyl-4-isothiazolin-3-one |

TABLE 3

Names of Compounds of Examples 2-7

| Example | Compound |
|---|---|
| 2 | N-benzyl-cis-3-thio-(1-acetylpropan-2-on-1-yl)acrylamide |
| 3 | N-(beta-phenethyl)-cis-3-thio-(1-acetylpropan-2-on-1-yl)-acrylamide |
| 4 | N-(p-chlorobenzyl)-cis-3-thio-(1-acetylpropan-2-on-1-yl)-acrylamide |
| 5 | N-phenyl-2-methyl-3-chloro-cis-3-thio-(1-acetylpropan-2-on-1-yl)acrylamide |
| 6 | N-(p-chlorophenyl)-3-chloro-cis-3-thio-(1-acetylpropan-2-on-1-yl)acrylamide |
| 7 | N-(p-chlorophenyl)-2-methyl-cis-3-thio-(1-acetylpropan-2-on-1-yl)acrylamide |

TABLE 4

Substituents for Examples 8-13

$$\begin{array}{c} Z_1 \quad\quad Z_2 \\ \diagdown C = C \diagup \\ Q-S \quad\quad C-NHR_1 \\ \quad\quad\quad \| \\ \quad\quad\quad O \end{array}$$

| Example | R₁ | Z₁ | Z₂ | Q |
|---|---|---|---|---|
| 8 | 4-CH₃-phenyl | —Cl | —CH₃ | —CH(COCH₃)₂ |
| 9 | —CH₂CH₂—(2-ethylphenyl) | —Cl | —Cl | —CH(COCH₃)₂ |
| 10 | —CH₂—(3-methylphenyl) | —Cl | —CH₃ | —CH(COCH₃)₂ |

TABLE 5

Names of Compounds of Examples 8-10

| Example | Compound |
|---|---|
| 8 | N-(p-tolyl)-2-methyl-3-chloro-cis-3-thio-(1-acetylpropan-2-on-1-yl) acrylamide |
| 9 | N-[beta-(o-ethylphenethyl)]-2,3-dichloro-cis-3-thio-(1-acetylpropan-2-on-1-yl)acrylamide |
| 10 | N-(m-methylbenzyl)-2-methyl-3-chloro-cis-3-thio-(1-acetylpropan-2-on-1-yl)acrylamide |

EXAMPLE 11

Biocidal Activity of Compounds

The compounds of Examples 1 and 5 were subjected to the following biocidal activity test procedures, with the results as indicated in Table 6.

The Speed of Kill (SOK) Test measures the loss of cell viability in an aqueous suspension of bacterial cells during a four hour period when these cells are contacted with a defined concentration of the test compound in synthetic hard water (SHW). A stock solution or dispersion of the test compound, typically at a concentration of 1%, is made in a 5:3:2 solvent solution of acetone, methanol, and water. The SHW is made by taking one liter of sterile deionized water and adding the following solutions to it:

1. 2 ml of a solution of 31.74 g of MgCl₂ and 73.99 g of CaCl₂ in 1000 ml. of sterile distilled water which has been heat sterilized.

2. 4 ml of a solution of 56.03 g of NaHCO₃ in 1000 ml of water which has been filter sterilized.

The combined solution is then filter sterilized to yield the SHW. A volume of the stock solution is dispensed into the SHW to give an initial test compound starting concentration of 500 ppm.

When the test is ready to be run, each vessel in the dilution series, except the first vessel, contains an equal volume of the SHW mixture with the test compound. The first vessel contains twice the volume of SHW with the starting concentration of test compound. One half of the SHW from the first vessel is transferred to the second vessel. After being mixed, one half the resulting volume is removed from the second vessel and transferred to the third vessel. The entire cycle is repeated sufficiently to give a series of concentrations amounting to 500, 250, 125, 63, 31, 16, 8, and 4 ppm, respectively.

Each vessel is then inoculated with a cell suspension of *Pseudomonas fluorescens* bacteria. The bacteria were grown on a 1% agar slant tube and incubated for 18–24 hours at 30° C. Thereafter, the tube is washed with 4 ml of sterile water. This wash is diluted to a density of 60 to 80 Nephelometer Turbidity Units (NTU). To 100 ml of the SHW containing the various concentrations of the test compound is added 0.75 ml of inoculum from the 60–80 NTU wash with good mixing. After 4 hours from the time of addition at 30° C., 5 µl of solution is transferred to 100 µl of a broth solution in order to recover any living cells. This mixture is incubated for 24 hours at 30° C. before noting the concentration in ppm at which each compound killed >99.999% of the cells in the SHW solution.

A minimum inhibitory concentration (MIC) value is obtained using a broth, two-fold serial dilution test performed as follows: A stock solution or dispersion of the test compound, typically at a concentration of 1%, is made in a 5:3:2 solvent solution of acetone, methanol, and water. A volume of the stock solution is dispensed into culture media to give an initial starting test concentration of 500 ppm compound.

When the test is ready to be done, each vessel in the dilution series, except the first vessel, contains an equal volume of compound free broth. The first vessel contains twice the volume of broth with the starting concentration of test compound. One half of the broth from the first vessel is transferred to the second vessel. After being mixed, one half the resulting volume is removed from the second vessel and transferred to the third vessel. The entire cycle is repeated sufficiently to give a series of concentrations amounting to 500, 250, 125, 63, 31, 16, 8, and 4 ppm, respectively.

Each vessel is then inoculated with a cell suspension of the appropriate test organism. Bacteria are grown in broth and fungi on agar slants for a time and at a temperature appropriate to the species being tested. At the end of the growth period, the broth is vortexed to disperse the cells. In the case of fungi, the spores are harvested by pipetting water onto the slant and dislodging the spores with a sterile loop. The cell/spore suspension is standardized by controlling incubation time, temperature, and the volume of the diluent. The suspension is then used to inoculate the vessels containing the broth compound. The vessels are then incubated at the appropriate temperature. After the incubation, the vessels are examined for growth/no growth. The minimum inhibitory concentration (MIC) is defined as the lowest concentration of compound that results in complete inhibition of growth of the test organism.

The organisms tested to demonstrate biocidal activity include:

BACTERIA:

*Pseudomonas fluorescens* (Ps.fl), gram negative
*Pseudomonas aerugenosa* (Ps.ae), gram negative
*Escherichia coli* (E.c), gram negative
*Staphylococcus aureus* (S.a), gram positive FUNGI:
*Aspergillus niger* (A.n)
*Aureobasidium pullulans* (A.p)

TABLE 6

| | SOK and MIC Test Results in Ppm | | | | | | |
|---|---|---|---|---|---|---|---|
| Example | SOK | Ps.fl | PS.ae | E.c | S.a | A.n | A.p |
| 1 | 32 | <4 | <4 | <4 | <4 | <4 | <4 |
| 5 | <4 | <4 | 8 | <4 | <4 | <4 | 32 |

The compounds of Examples 1–7 were subjected also to the following alternate biocidal activity test procedures, with the results as indicated in Table 7.

SPEED OF KILL TEST

The SOK test measures the viability of Pseudomonas fluorescens inoculum in synthetic hard water (SHW) when exposed for 24 hours to a 100 ppm acetone solution of a given compound.

An acetone solution of the compound was prepared at 10,000 ppm and 0.1 ml was added to 9.8 ml of SHW. 0.1 ml of Ps fl inoculum at 10,000,000 cells per ml was added to the SHW, providing 10 ml of solution which was incubated for 24 hours prior to recovery into Tryptic Soy Broth (TSB).

To recover and measure the living cells, 2.5 ml of the SHW mix was transferred to a reservoir from which 2.5 µl was then transferred 8 times to microtiter wells containing 225 µl of TSB. Each of the 8 transfers was then serially diluted seven times, providing eight replicates of eight dilutions. The concentration at which no living cells were recovered was used to back calculate the log reduction. The data was entered into the database, and the log reductions calculated automatically.

MINIMUM INHIBITORY CONCENTRATION TEST

The MIC test measures the viability of *Pseudomonas fluorescens* inoculum in TSB when exposed for 72 hours to varying concentrations of test compound.

A 125 µl aliquot of 10,000 ppm test compound in acetone was added to 4.88 ml of TSB to provide a 250 ppm solution. From this solution, 100 µl was transferred to the first row of two microtiter plate columns. Both replicates and five additional compounds were all serially diluted 1:1 to a final concentration of 0.8 ppm in TSB.

Inoculation was accomplished by diluting a 24 hr Ps fl culture, four mls per 36 mls of phosphate buffer solution. A Dynatech autoinoculator was used to transfer 1.5 µl of this cell suspension to the microtiter plates. The plates were incubated at 30° C. for 3 days before the lowest concentration at which no growth occurs was recorded in the database.

The SOK data and MIC test data on Ps.fl, Ps.ae, E.c, and S.a bacteria and Candida albicans (C.alb), A.n and A.p fungi are listed in Table 8.

TABLE 7

| | SOK and MIC Test Results in Ppm | | | | | | | |
|---|---|---|---|---|---|---|---|---|
| Compound of Ex. | SOK | A.n | A.p | C.alb | E.c | Ps.ae | Ps.fl | S.a |
| 1 | 1-100 | 4-8 | <4 | <4 | <4 | 8 | 4-16 | <4 |
| 2 | 100 | 125-500 | 31 | 31-63 | 63-125 | 500 | >500 | 31 |
| 3 | 100 | 63-500 | 8-16 | 31 | 250 | >500 | >500 | 63 |

TABLE 7-continued

| | SOK and MIC Test Results in Ppm | | | | | | | |
|---|---|---|---|---|---|---|---|---|
| Compound of Ex. | SOK | A.n | A.p | C.alb | E.c | Ps.ae | Ps.fl | S.a |
| 4 | >100 | 31-500 | 16 | 63 | 63 | >500 | >500 | 31 |
| 5 | >100 | <4 | 16 | 16 | <4 | 16-31 | 16 | 8 |
| 6 | >100 | >500 | * | * | * | * | >500 | * |
| 7 | >100 | 31-63 | 4-8 | 16 | 63-125 | >500 | >500 | 125 |

*Test not run.

EXAMPLE 12

The compounds of Examples 1 to 7 were subjected to the following fungicides test with the results as indicated in Table 8.

DESCRIPTION OF FUNGICIDE TEST METHODS

The compounds of Examples 1 to 7 were tested for fungicidal activity in vivo against cucumber downy mildew (CDM), rice blast (RB), rice sheath blight (RSB), tomato late blight (TLB), wheat powdery mildew (WPM), wheat stem rust (WSR) and wheat leaf rust (WLR). In tests on cereals (except for rice plants used for testing rice blast), the plants were trimmed about 24 hours prior to the application of the fungicide compound to provide a uniform plant height and to facilitate uniform application of the compound and inoculation with the fungus. The compounds were dissolved in a 2:1:1 mixture of water, acetone, and methanol, sprayed onto the plants, allowed to dry (four to six hours), and then the plants were inoculated with the fungus. Each test utilized control plants which were sprayed with the water, acetone, and methanol mixture and inoculated with the fungus. The remainder of the technique of each of the tests is given below and the results are reported as percent disease control (percentages of plants treated with the compounds of the present invention lacking disease signs or symptoms compared to the untreated control plants).

CUCUMBER DOWNY MILDEW (CDM)

*Pseudoperonospora cubensis* was maintained on leaves of live Marketer cucumber plants in a constant temperature room at 65° F. to 75° F. in humid air with moderate light intensity for 7 to 8 days. A water suspension of the spores from infested leaves was obtained and the spore concentration was adjusted to about 100,000 per ml of water. Marketer cucumber seedlings were inoculated by spraying the underside of the leaves with a DeVibiss atomizer until small droplets were observed on the leaves. The inoculated plants were incubated in a mist chamber for 24 hours at about 70° F. and then subsequently incubated for 6 to 7 days in a controlled temperature room under mist at 65° F. to 75° F. Seven days after inoculation, the percent disease control was determined.

RICE BLAST (RB)

Nato rice plants were inoculated with *Piricularia oryzae* (about 20,000 conidia per ml) by spraying the leaves and stems with an airbrush until a uniform film of inoculum was observed on the leaves. The inoculated plants were incubated in a humid environment (75° F. to 85° F.) for about 24 hours, then placed in a greenhouse environment (70° F. to 75° F.). Seven to eight days after inoculation, the percent disease control was determined.

RICE SHEATH BLIGHT (RSB)

*Pellicularia filamentosa* (f. sp. sasiki) was cultured on an autoclaved mixture of crushed rice seeds and potato dextrose broth (100 gm of rice seeds per 30 ml of potato dextrose broth) in a 500 ml Erlenmeyer flask. After 10 days, the culture was blended in a blender to produce a uniform inoculum. Approximately one teaspoon of inoculum was spread among Lebonnet rice seedlings on the soil surface of each pot (3 inch diameter). The inoculated seedlings were incubated for 5 days in a humidity cabinet (85° F. to 90° F.). Percent disease controls were determined immediately after removing the seedlings from the cabinet.

TOMATO LATE BLIGHT (TLB)

*Phytophthora infestans* was cultured on four week old Pixie tomato plants in a controlled environment room (65° F. to 70° F. and 100% relative humidity). After storage, the spores were washed from the leaves with water and dispersed by DeVilbiss atomizer over three week old Pixie tomato plants which had been sprayed previously with experimental fungicides. The inoculated plants were placed in a humidity cabinet at 70° F. and constant mist for 24 hours for infection. The plants were then moved to the controlled environment room as above and scored after three more days incubation. Disease control levels were recorded as percent control four days after inoculation and five days after spraying the compounds.

WHEAT POWDERY MILDEW (WPM)

*Erysiphe graminis* (f. sp. tritici) was cultured on Pennol wheat seedlings in a controlled temperature room at 65° F. to 75° F. Mildew spores were shaken from the culture plants onto Pennol wheat seedlings which had been sprayed previously with the fungicide compound. The inoculated seedlings were kept in a controlled temperature room at 65° F. to 75° F. and subirrigated. The percent disease control was rated 8 to 10 days after the inoculation.

WHEAT STEM RUST (WSR)

*Puccinia graminis* (f. sp. tritici Race 15B-2) was cultured on Wanzer wheat seedlings for a period of 14 days in a greenhouse. A water suspension of the spores from infested plants was obtained and the spore concentration was adjusted to about 200,000 spores per ml of deionized water. Wanzer wheat plants which had been previously treated with the fungicide compounds were inoculated by applying the stem rust spore suspension, until runoff, with a DeVilbiss atomizer at 5 lbs. per square inch air pressure. After inoculation, the plants were placed in a humid environment at approximately 75° F. where they were exposed to 12 hours of continuous darkness followed by a minimum of 3 to 4 hours of light having an intensity of about 500 footcandles. The temperature in the chamber did not exceed 85° F. At the end of the light period, the plants were placed in a greenhouse where they were permitted to grow for a period of two weeks at which time the percent disease control was determined.

WHEAT LEAF RUST (WLR)

*Puccinia recondita* (f. sp. tritici Races PKB and PLD) was cultured on seven day old wheat (cultivar Fielder) over a 14 day period in the greenhouse. Spores were collected from the leaves with a cyclone vacuum or by settling on aluminum foil. The spores were cleaned by sieving through a 250 micron opening screen and stored or used fresh. Storage employed sealed bags in an Ultralow freezer. When stored, spores must be heat shocked for two minutes at 40° F. before use. A spore suspension is prepared from dry uredia by adding 20 mg (9.5 million) per ml of Soltrol oil. The suspension is dispensed into gelatin capsules (0.7 ml capacity) which attach to the oil atomizers. One capsule is used per flat of twenty of the two inch square pots of seven day old Fielder wheat. After waiting for at least 15 minutes for the oil to evaporate from the wheat leaves, the plants are placed in a dark mist chamber (18°-20° C. and 100% relative humidity) for 24 hours. The plants are then put in the greenhouse for the latent period and scored after 10 days for disease levels. Protective and curative tests were inoculated one day after and two days, respectively, before spraying the plants with the test chemicals.

TABLE 8

| | % Control* vs. Assorted Fungi | | | | | | |
|---|---|---|---|---|---|---|---|
| Example | CDM | RB | RSB | TLB | WPM | WSR | WLR |
| 1 | 100/200 | 80/200 | 0/300 | 90/300 | 0/300 | 70/300 | —/— |
| 2 | 70/300 | 0/300 | 0/300 | 0/300 | 0/300 | 40/300 | —/— |
| 3 | 90/200 | 94/200 | 0/300 | 20/300 | 0/300 | 40/300 | —/— |
| 4 | 95/300 | 89/200 | 0/300 | 15/300 | 0/300 | 30/300 | —/— |
| 5 | 49/100 | 50/100 | ** | 35/100 | 0/300 | 50/100 | —/— |
| 6 | 85/100 | 50/100 | 0/100 | 0/100 | 0/100 | —/— | 50/100 |
| 7 | 0/100 | 50/100 | 0/100 | 0/100 | 60/100 | —/— | 50/100 |

*Values Given as % Control/Ppm Application Rate
**Test did not replicate
—/— = test not run While the invention has been described in sufficient detail for those skilled in the art to be able to make and use it, various alternatives, modifications, and improvements should become apparent from the forgoing disclosure without departing from the spirit and scope of the invention.

I claim:

1. A compound of the formula

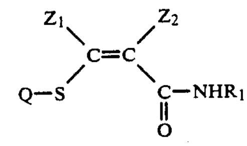

I wherein $R_1$ is selected from phenyl, phenethyl and benzyl, each optionally substituted with chloro or $C_1$-$C_4$-alkyl, Q is 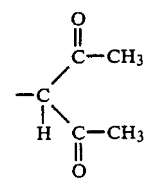 and $Z_1$ and $Z_2$ are independently selected from hydrogen, halogen and ($C_1$-$C_4$) alkyl.

2. Compound of claim 1 wherein $Z_1$ is halo.

3. Compound of claim 1 wherein $Z_1$ is chloro and $Z_2$ is methyl.

4. Compound of claim 1 wherein $R_1$ is selected from phenyl and 4-chlorophenyl.

5. Compound of claim 2 wherein $R_1$ is selected from phenyl and 4-chlorophenyl.

6. Compound of claim 3 wherein $R_1$ is selected from phenyl and 4-chlorophenyl.

7. A composition comprising a compound of claim 1 in a fungicidally-effective amount and in an agronomically acceptable carrier.

* * * * *